United States Patent [19]
Cron et al.

[11] Patent Number: 6,024,093
[45] Date of Patent: Feb. 15, 2000

[54] PROPRIOCEPTIVE SOLE OR PEDAL DEVICE CONTAINING CRYSTALS FOR TREATMENT OF STATURAL DISORDERS

[75] Inventors: Christophe Cron, Deroche; Thierry Pautrot, Carignan; Thierry Abribat, Montréal, all of Canada

[73] Assignee: Asana Laboratories Inc., Quebec, Canada

[21] Appl. No.: 09/180,213

[22] PCT Filed: May 1, 1997

[86] PCT No.: PCT/CA97/00303

§ 371 Date: Feb. 8, 1999

§ 102(e) Date: Feb. 8, 1999

[87] PCT Pub. No.: WO97/41819

PCT Pub. Date: Nov. 13, 1997

[51] Int. Cl.[7] .................................................. A61B 19/00

[52] U.S. Cl. ................................................. 128/897; 36/43

[58] Field of Search ................................. 36/43, 141, 91, 36/153; 128/897, 898; 607/1, 88

[56] References Cited

U.S. PATENT DOCUMENTS 5,158,526 10/1992 Bricot ......................................... 600/9

*Primary Examiner*—Linda C. M. Dvorak
*Assistant Examiner*—Rosiland Kearney
*Attorney, Agent, or Firm*—Klauber & Jackson

[57] ABSTRACT

An article such as a sole or a shoe adapted to contact the sole of a foot, which incorporates at least one crystalline substance which is capable of developing a color in the wavelength range between about 400 nm and 900 nm and stimulates the reflex zones located at the sole of the foot. The method of utilizing such article is also disclosed.

25 Claims, 3 Drawing Sheets

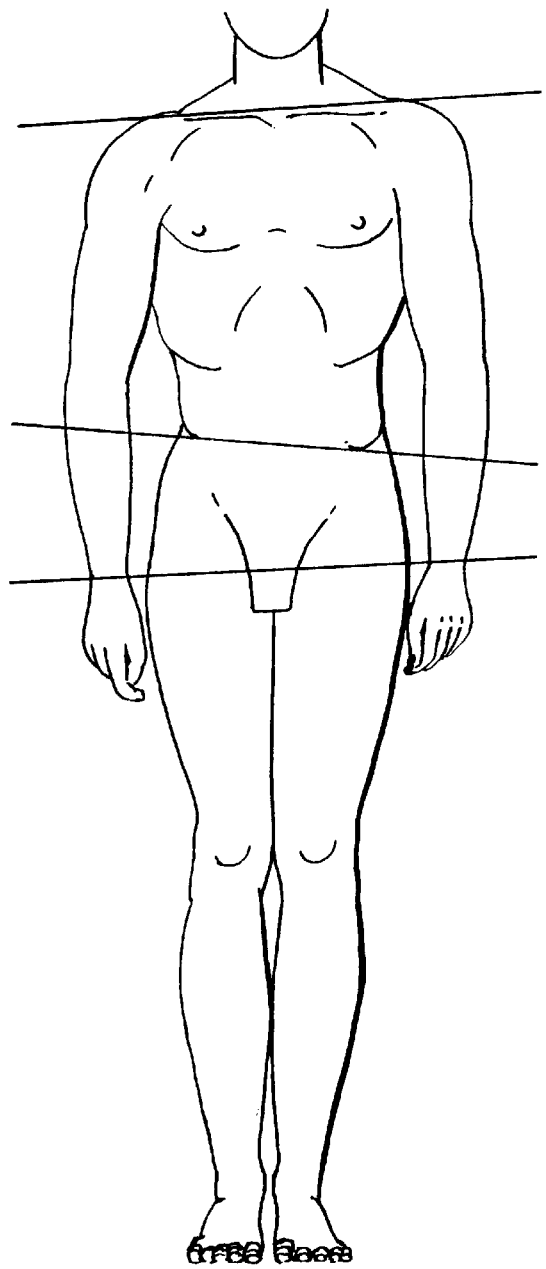
*Fig.*2
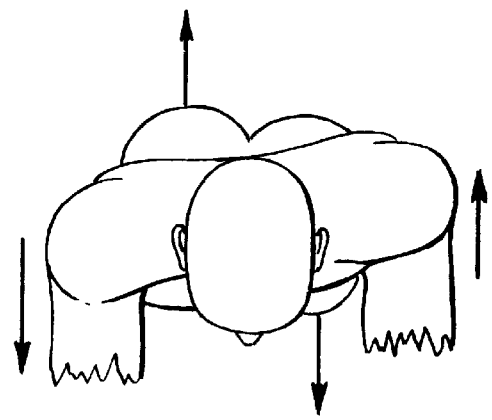
*Fig.*1 a P<0.02 when compared to pre-treatment vlue
b P<0.05 when compared to placebo

PROPRIOCEPTIVE SOLE OR PEDAL DEVICE CONTAINING CRYSTALS FOR TREATMENT OF STATURAL DISORDERS

BACKGROUND OF THE INVENTION (a) Field of the Invention

The present invention relates to medical devices and a therapeutic method for the treatment and the prevention of physical troubles associated with a statural disequilibrium.

(b) Description of Prior Art

A major part of the chronic pains of the back or of the neck are caused by spine disequilibrium. This disequilibrium is clinically associated with unbalances or rotations of the pelvic and pectoral girdles.

It has been documented that less than 10% of the population has perfectly balanced pelvic and pectoral girdles, i.e., an equilibrated spine. Those individuals almost never experience back or neck chronic pain in their life span, and are rarely prone to arthrosis. Constitutive or acquired unbalances occur in the remaining 90% of the population, in whom spine curvatures and intervertebral angles are non-physiologic, leading to pain, sequentially at the muscular, articular and ultimately the bone level.

Spine disequilibrium may also be responsible for various disorders, including muscular and articular pains, vertigos, lumbagos, arthrosis. The link between these disorders and the spine was established based on observations that correction of the pelvic and pectoral girdles unbalances resulted in improvements of the symptoms.

Various therapeutic approaches have been developed to restore the spine equilibrium, and thus alleviate chronic pains in patients. Most of these approaches involve the design of pedal devices, mainly soles, since the feet are the points of normal support of the body in human. In fact, it has been proven that the feet are the origin of ascending neural proprioceptive chains that control the tonus of the statural muscular system, of which the spine muscles are one component. Adequate stimulations of particular reflex zones located on the sole of the feet induce a realignment of the ascending proprioceptive chains, and thus a re-equilibration of the skeletal muscular system.

This concept has previously been verified by the design of the following types of soles:

soles with micro-reliefs located at the level of the reflex zones of the foot have been used for several years. However, the routine use of this type of sole is hampered by the fact that the micro-reliefs have to be very meticulously adjusted for each patient, and their precise thickness must be regularly modified. In addition, they are only active when the patient is in a standing position.

soles incorporating a polarizing substance, such as a polarizing or polarizer plate have been described in U.S. Pat. No. 5,158,526. These soles have been marketed in Europe for several years and have been used for the correction of statural disorders. However, they exhibit some major drawbacks, that limit their routine clinical use. Namely, they need to be applied continuously directly at the contact of the skin of the foot sole, their efficacy being almost completely abolished when fabrics such as nylon or stained cotton, found in socks or stockings, are placed between the device and the skin. This continuous application induces increased perspiration in most of the patients, which makes them uncomfortable to wear, resulting in a poor patient's compliance. In addition, the lifetime of the active principles of these soles (superposed polarizer plates) is limited to several months, requiring a regular monitoring of the device's efficacy.

a similar kind of soles incorporating at least one flexible filtering film with a determined spectral transmission curve have been described in Canadian patent No. 1,328,734.

Although several case reports have described the efficacy of the aforementioned types of soles, there exist no data from controlled clinical studies performed to establish their clinical usefulness. Despite the fact that anecdotal research, such as case reports, may provide some valuable information on the activity of a product, it is widely recognized by the scientific and medical communities that only placebo-controlled, double blind studies can help to fully objectively assess the efficacy and the safety of such a medical device, especially when the parameters used to measure efficacy are essentially clinical, qualitative or semi-quantitative parameters.

Therefore, it is an object of the present invention to provide a pedal device, such as a sole, a shoe or another pedal apparatus, that would allow to rapidly correct spine disequilibrium, and thus alleviate associated physical disorders, such as chronic back or neck pains.

It is another object of the invention to provide a type of sole that could exert a therapeutic effect when worn under socks or stockings, in order to prevent patient's discomfort, and therefore improve compliance.

It is also an object of the invention to provide a type of sole, of which the active principles would have a long lifetime, in order to avoid the need for frequent monitoring of the quality of the sole.

It is also an object of the invention to provide a type of sole with a clinical efficacy proven by data resulting from placebo-controlled, double-blind studies.

SUMMARY OF THE INVENTION

The invention relates to a pedal device for treating and/or preventing physical troubles associated with statural disequilibrium which comprises an article adapted to contact the sole of a foot, characterized in that the article incorporates at least one crystalline substance having a color by emitting photons in the wavelength range between about 400 nm and 900 nm and stimulating reflex zones located at the sole of a foot.

The invention therefore has for its object a pedal device, such as a sole, a shoe or any other pedal apparatus, preferably incorporating one or several types of selected crystals such as minerals possibly in powder form, placed, for example, at designated reflex zones of the foot sole.

The invention also relates to a therapeutic method consisting in using the aforementioned device to achieve a partial or complete restoration of the spine physiological alignment, and therefore prevent or cure physical disorders associated with spine disequilibrium such as musculoskeletal pain.

The invention also relates to a therapeutic method consisting in using the aforementioned device as a therapeutic agent to improve the condition of patients suffering from musculoskeletal pain, such as chronic back pain associated or not with spine disequilibrium.

The active principle of the sole or of the pedal device may be a combination of one or several crystalline substances. Both the type and amount of crystalline substances to be used, alone or in combination, are selected based on their ability to stimulate the reflex zones located at the sole of the foot. Although the exact mechanism involved in alleviating musculoskeletal pains associated or not with spine disequilibrium and troubles associated with statural disequilibrium is not well understood, it is believed that these crystalline substances produce natural frequencies and radiations which affect the reflex zones. If the crystalline substances are minerals, they cab be mono-, bi-, or multi-atomic, preferably in the form of powders or crystals. They may be selected from the following groups which are listed as illustrative examples:

elements in crystal or powder forms, such as diamond (C), gold (Au), copper (Cu), platinum (Pt), sulfur (S or $S_8$), silver (Ag), or bismuth (Bi);

natural and synthetic sulphides and sulphosalts in the form of crystals or powders, such as argentite (AgS), arsenopyrite (FeAsS), arsenic trisulfide ($As_2S_3$), proustite ($Ag_3AsS_3$), pyrite ($FeS_2$);

natural and synthetic halides in the form of crystal or powders, such as fluorite ($CaF_2$) or cryolite ($Na_3AlF_6$);

natural and synthetic oxides and hydroxides in the form of crystals or powders, such as silicon dioxide ($SiO_2$) derivatives (quartz, jasper, topaz safranite, cornelian, aventurine, amethyst, chalcedony, agate, crystobalite, flint, sand, tridymite) or rutile ($TiO_2$);

natural and synthetic nitrates, carbonates and borates in the form of crystals or powders, such as malachite ($Cu_2[(OH)_2CO_3]$), azurite ($Cu_3[OH/CO_3]$), cerusite ($PbCO_3$);

natural and synthetic sulfates, chromates, molybdates and tungstates in the form of crystals or powders, such as crocoite ($PbCrO_4$) or anglesite ($PbSO_4$);

natural and synthetic phosphates, arseniates and vanadates in the form of crystals or powders, such as apatite ($Ca_5[F(PO_4)_3]$);

natural and synthetic silicates in the form of crystals or powders, such as Feldspars ($AlSi_3O_8$ and $AlSi_2O_6$ derivatives), micas ($AlSi_3O_{10}$ and $Si_4O_{10}$ derivatives);

natural and synthetic organic substances in the form of crystals or powders, such as amber ($C_{1016}O$) or aurin ($C_{19}H_{14}O_3$).

The pedal device according to the invention consists in a pedal support device which may incorporate selected crystals or powders (the active principle). The crystals or powders can be inserted either inside or at the surface of the device, provided they are at the level of the sole.

The therapeutic method according to the invention consists in applying the pedal device, either at one or at both feet of the patient, in order to induce the expected therapeutic effect. According to this therapeutic method, the active principle (e.g., the crystals or powders), possibly due to the natural frequencies and radiations they give out, exert a non-toxic stimulatory action on the reflex zones located at the level of the sole skin, thereby stimulating the proprioceptive ascending chains, and inducing an harmonization of the tonus of the statural muscular system. The observed therapeutic effects include the followings:

a rapid re-equilibration of the spine towards normalization of spine curvatures and intervertebral angles, which can be clinically evidenced by disappearance of unbalances and rotations of the pelvic and scapular girdles.

the relief of symptoms associated with spine disequilibrium, including chronic back and neck pains, other muscular and articular pains, vertigos, lumbagos, arthrosis.

the prevention of the occurrence of the aforementioned disorders associated with spine disequilibrium.

an energetic action, including an increase of physical performances and a diminution of the stress level.

The device according to the invention is notable for the fact that it can exert its therapeutic effect whether applied directly at the contact of the skin of the foot sole or under socks or stockings, made of any type of fabric, which improves patient's comfort and compliance. It is also notable for the fact that its active principle (e.g., the crystals or powders) have an unlimited lifetime, which eliminates the need to frequently monitor the quality of the device. In addition, since the crystals or powders used are naturally occurring on earth, no toxic effect can result from the energy, frequencies or radiations they give out.

BRIEF DESCRIPTION OF THE DRAWING

This invention is illustrated by means of the annexed drawings which are given only for the purpose of illustration and without restriction. In the drawings, FIG. 1 is an illustration of the rotation of the pectoral and pelvic girdle;

FIG. 2 is an illustration of the unbalance of the pelvic and pectoral girdles;

DESCRIPTION OF PREFERRED EMBODIMENTS

Two examples of rotations and unbalances are illustrated respectively in FIG. 1 and FIG. 2. FIG. 1 deals with an improper rotation of the pectoral and pelvic girdle and FIG. 2 shows an unbalance of the pelvic and pectoral girdles.

According to a preferred embodiment, the crystalline substance used as active principle in the pedal device is sulphur in the powder form. According to another preferred embodiment, the active principle is a combination of seven types of crystals or powders, namely red jasper, cornelian, topaz safranite, aventurine, azurite, amethyst and white quartz. According to another preferred embodiment, the active principle is a combination of sulphur in the powder form and the seven minerals previously mentioned in the form of crystals.

Figure 3:
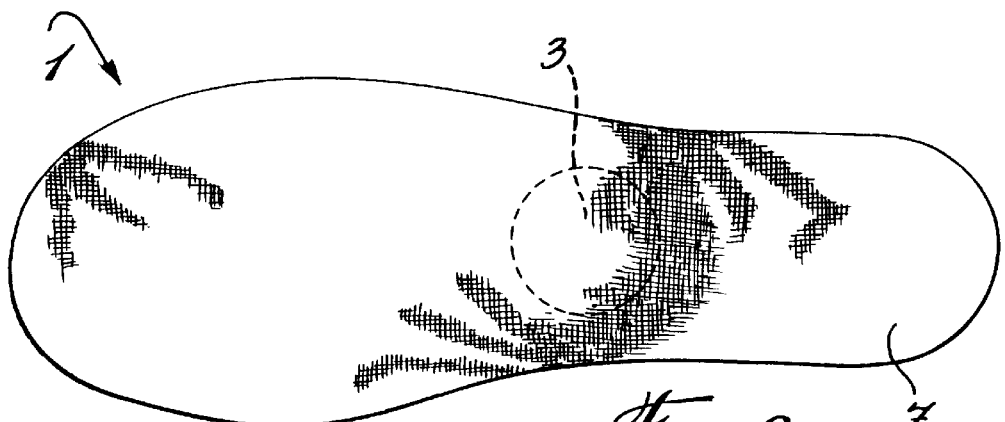
FIG. 3 is a top view of a sole according to the invention including sulphur powder between the two semi-rigid fabric layers.
Figure 4:
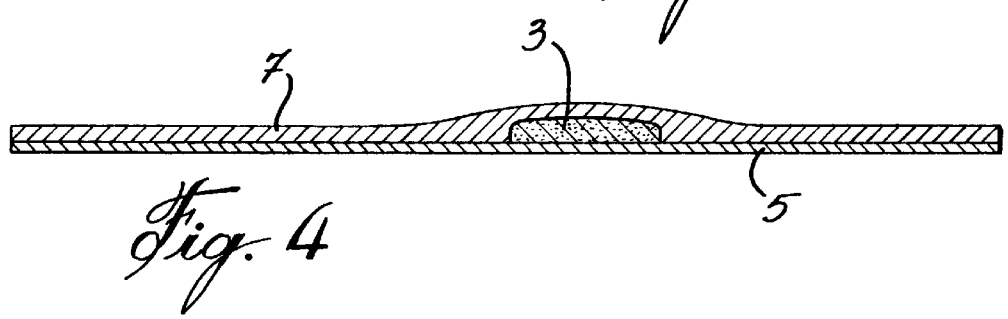
FIG. 4 is a longitudinal cross-section view of the sole illustrated in FIG. 3.

According to a highly preferred embodiment, the pedal device is a sole 1, in which an amount of 5 mg to 30 g of sulphur powder 3 is incorporated at the level of the arch, between the two semi-rigid fabric layers 5 and 7 used to manufacture the sole, as shown in FIGS. 3 and 4 of the drawings.

According to another highly preferred embodiment the pedal device is a sole in which a combination of seven crystals with defined colors (one red, one orange, one yellow, one green, one blue, one purple, and one white) is inserted between the two semi-rigid fabric layers used to manufacture the sole.

Figure 5:
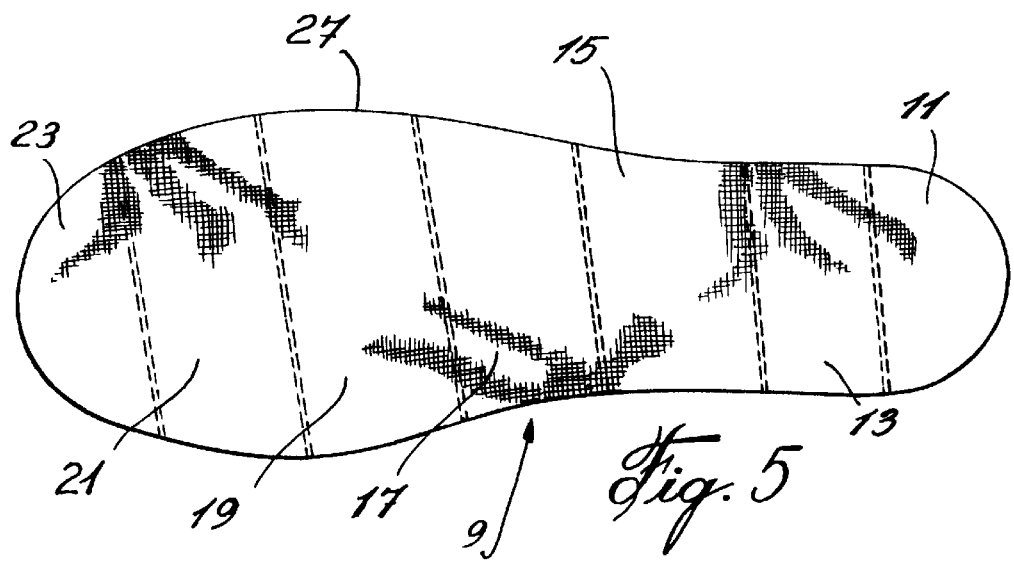
FIG. 5 is a top view of a sole according to the invention including transverse bands of seven different minerals.
Figure 6:
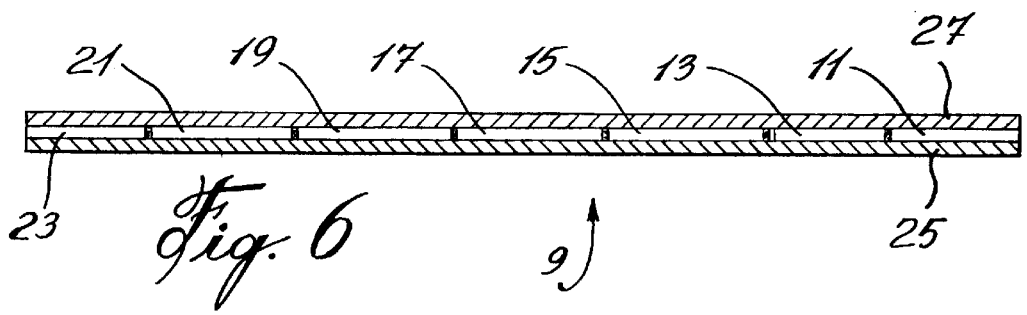
FIG. 6 is a longitudinal cross-section view of the sole illustrated in FIG. 5.

According to another highly preferred embodiment, the pedal device is a sole 9, in which a combination of seven different crystals or powders with selected colors (red jasper 11, orange cornelian 13, yellow topaz safranite 15, green aventurine 17, blue azurite 19, purple amethyst 21 and white quartz 23) is inserted as seven bands transversely between the two semi-rigid fabric layers 25, 27 used to manufacture the sole, as shown in FIGS. 5 and 6 of the drawings.

According to another highly preferred embodiment, the pedal device is a sole, in which both the sulphur powder and the combination of the seven crystals are incorporated.

The present invention will be more readily understood by referring to the following examples which are given to illustrate the invention rather than to limit its scope.

EXAMPLE I

Effects of soles containing sulphur vs. soles with polarizing Polaroid™ plates on patient's stature: placebo-controlled, double-blind studies The goal of this study was to assess the efficacy of sulphur-containing soles and to compare it to that of soles containing a previously described (U.S. Pat. No. 5,158,526) active principle, i.e., superposed polarizing plates. Efficacy was judged clinically by the ability of tested soles to correct unbalances and rotations of the pectoral and the pelvic girdles. In study A, soles were tested immediately at the contact of the feet skin, whereas in study B, soles were tested under socks. Both studies were run in a double-blind fashion vs. a placebo sole, in order to prevent any subjective component in the course of the clinical evaluation.

Materials and Methods
Patients

A total of 40 patients (24 in study A and 16 in study B) were included in the protocols. Selected patients ranged between 18 and 65 years of age, and had unbalances of the pectoral and of the pelvic girdles, as evidenced in an initial clinical evaluation. None of them had received any kind of medical sole in the previous 6 months.

Treatments

Three pairs of soles were designed for the needs of the present studies. The first one was a sole, in which an amount of 50 to 100 mg of sulphur powder was incorporated at the level of the arch, between the two semi-rigid fabric layers used to manufacture the sole, according to one of the preferred embodiment of the present invention. The second one was a sole made with the active principle (superposed Polaroid™ plates) commercialized by the company Statipro (Marseille, France), according to U.S. Pat. No. 5,158,526. Finally, the third one was a placebo sole, made, as the other test soles, by gluing together two semi-rigid leather layers, but with no active principle placed between both layers at the level of the arch.

Experimental procedures

Both studies A and B were prospective, placebo-controlled, double-blind studies. Each selected patient was subjected to 3 consecutive treatments in study A and 4 consecutive treatments in study B. Each treatment consisted in applying a pair of soles, together with a pair of socks and a pair of shoes to the feet of the patient, according to the following experimental plan:

Study A
  Treatment 1: placebo sole, in contact with the foot skin
  Treatment 2: polarizing sole, in contact with the foot skin
  Treatment 3: sulphur sole, in contact with the foot skin
Study B
  Treatment 1: placebo sole, under the socks
  Treatment 2: polarizing sole, under the socks
  Treatment 3: sulphur sole, under the socks
  Treatment 4: sulphur sole, in contact with the foot skin
The blindness of the studies was ensured by the following procedures:

the treatments and the clinical evaluation were performed by two different persons, located in different rooms. In these conditions, the clinician performed clinical evaluations on patients wearing shoes and socks, ensuring the blindness of the clinical examination. In addition, all three types of soles were indistinguishable and coded, so that the technician responsible for the treatments could not know the nature of the sole he was using. Finally, in each study, all 3 or 4 treatments were administered in a random sequence, differing for each patient.

Clinical evaluation

Following each treatment, the patient was subjected to a clinical evaluation, that included:
  pelvic girdle unbalance: detected by a visual examination and a palpation of the pelvis;
  pectoral girdle unbalance: detected by a visual examination and palpation of the shoulders, and quantified by the following test: patient in standing position, both arms dangling, the clinician joins both hands and measures the distance (cm) between both forefingers;
  pectoral girdle rotation: detected and quantified by the following test: patient in standing position, raises both arms parallel, the clinician joins both hands and measures the distance (cm) between both forefingers.

Statistical Analysis

The relative efficacies of the different treatments within each study were evaluated by comparing:
  1—the effects of the treatments on the number of pelvic girdle unbalances, pectoral girdle unbalances and rotations completely corrected, by McNemar tests;
  2—the effects of the treatments on the intensities of pectoral girdle unbalances and rotations, by an ANOVA analysis of variance for repeated measures. When normality test did not pass, a repeated measure ANOVA on rank was run.

Results
Study A

As shown in Table I, the results revealed that both the polarizing and the sulphur soles completely resolved a similar number of unbalances and rotations when applied at the foot skin contact. Both treatments were significantly more efficient than the placebo treatment. However, as illustrated in Table II, the sulphur soles was significantly better than the polarizing soles ($P<0.05$) with respect to their effects on the intensities of the pectoral girdle unbalances and rotations. Namely, the polarizing soles decreased unbalances and rotations intensities by 61% and 73%, respectively, when compared to the placebo soles, whereas sulphur soles decreased unbalances and rotations intensity by 67% and 86%, respectively.

Study B

As shown in Tables III and IV, when applied under cotton socks, the polarizing soles had a very weak effect on statural parameters. These soles did not succeed in completely resolving unbalances or rotations except for 2 pelvic girdle unbalances (Table III). Moreover, they exhibited a very low potency, decreasing the intensities of pectoral girdle unbalances and rotations by 15% and 18% respectively. In contrast, the sulphur soles were equipotent, whether applied under socks or directly applied at the foot skin contact, and reduced the intensities of pectoral girdle unbalances and rotations by 72% and 72%, respectively, when applied under socks (Table IV). When applied under socks, the sulphur soles were statistically more potent than the polarizing soles with respect to all measured parameters (Tables III and IV).

In conclusion, the results of both these studies showed that the sulphur soles, which are one of the preferred embodiment of the present invention:

1) were more potent than the polarizing soles in improving statural parameters when applied directly at the contact of the foot skin; and 2) retained their full potency when applied under socks, in contrast to the polarizing soles, that lost almost completely their activity.

TABLE I

Study A: number of unbalances and rotations completely resolved following applications of the tested soles

|  | pelvic girdle unbalances | pectoral girdle unbalances | pectoral girdle rotations |
|---|---|---|---|
| placebo soles at the skin contact | 0 / 24 | 0 / 24 | 0 / 24 |
| polarizing soles at the skin contact | 18 / 24 (a) | 7 / 24 (a) | 13 / 24 (a) |
| sulphur soles at the skin contact | 20 / 24 (a) | 8 / 24 (a) | 17 / 24 (a) |

(a) $P < 0.05$ when compared to the placebo soles

TABLE II

Study A: effect of the tested soles on the intensity of pectoral girdle unbalances and rotations (mean ± SEM of 24 patients)

|  | pectoral girdle unbalances | pectoral girdle rotations |
|---|---|---|
| placebo soles at the skin contact | 2.06 ± 0.11 | 1.60 ± 0.12 |
| polarizing soles at the skin contact | 0.81 ± 0.13 (a) | 0.43 ± 0.11 (a) |
| sulphur soles at the skin contact | 0.68 ± 0.55 (a,b) | 0.23 ± 0.08 (a,b) |

(a) $P < 0.05$ when compared to the placebo soles
(b) $P < 0.05$ when compared to the polarizing soles

TABLE III

Study B: number of unbalances and rotations completely resolved following applications of the tested soles

|  | pelvic girdle unbalances | pectoral girdle unbalances | pectoral girdle rotations |
|---|---|---|---|
| placebo soles under socks | 0 / 16 | 0 / 16 | 0 / 16 |
| polarizing soles under socks | 2 / 16 | 0 / 16 | 0 / 16 |
| sulphur soles under socks | 12 / 16 (a,b) | 7 / 16 (a,b) | 8 / 16 (a,b) |
| sulphur soles at the skin contact | 11 / 16 (a,b) | 7 / 16 (a,b) | 7 / 16 (a,b) |

(a) $P < 0.05$ when compared to the placebo soles
(b) $P < 0.05$ when compared to the polarizing soles

TABLE IV

Study B: effects of the tested soles on the intensities of pectoral girdle unbalances and rotations (mean ± SEM of 16 patients)

|  | pectoral girdle unbalances | pectoral girdle rotations |
|---|---|---|
| placebo soles under socks | 1.98 ± 0.14 | 2.04 ± 0.17 |
| polarizing soles under socks | 1.68 ± 0.14 (a) | 1.68 ± 0.17 (a) |
| sulphur soles under socks | 0.56 ± 0.16 (a,b) | 0.58 ± 0.16 (a,b) |
| sulphur soles at the skin contact | 0.61 ± 0.17 (a,b) | 0.72 ± 0.20 (a,b) |

(a) $P < 0.05$ when compared to the placebo soles
(b) $P < 0.05$ when compared to the polarizing soles

EXAMPLE II

Effect of crystal-containing insoles on pain and quality of life in patients with chronic back pain: a randomized placebo controlled, double-blind study The objective of this clinical study was to determine the long-term beneficial effect of crystal-containing insoles in patients with chronic back pain. The tested insoles contained a combination of 8 different crystals of minerals as described in the preferred embodiments of the present invention.

With regards to the choice of parameters to measure to evaluate treatment efficacy, there is growing recognition that patient perspectives are essential. Back pain is one of many chronic or recurrent condition for which cure may be impossible, and improving quality of life is often the main goal of. therapy. Therefore, we evaluated the effect of a 6-week treatment with the crystal-containing insoles on patient's quality of life assessed by a validated questionnaire, specifically designed to measure self-rated disability due to back pain.

Materials and methods

Patients

A total of 35 patients were included in the protocol. Selected patients ranged between 18 and 65 years of age, and had chronic back pain, which was defined as back pain present on at least half of the days in a 12-month period in a single or in multiple episodes over the year. The patients were included in the study only if they had a score of at least 6 in the Roland and Morris questionnaire (see below for description). None of the patients had worn any kind of medical insole in the previous 6 months. All the patient gave informed consent to participate in the study.

Treatments

The patients were randomly as signed to two treatment groups in a 2:1 ratio ( 2 crystal insoles for 1 placebo sole) . The crystal-containing insoles were insoles in which a combination of seven different minerals with selected colors (red jasper, orange corralling, yellow topaz safranite, green aventurine, blue azurite, purple amethyst and white quartz) was inserted as seven lines transversely between the two semi-rigid fabric layers used to manufacture the sole, according to the drawings in FIGS. 5 and 6 of the present invention; in addition, an amount of 50 to 100 mg sulphur powder was placed at the level of the arch, according to FIGS. 3 and 4 of the present invention. The placebo soles were manufactured using the same raw materials, except for the crystals and sulphur powder, which were substituted by sugar. Both placebo and crystal insoles were indistinguishable and coded to ensure the blindness of the study.

Measures

On the day of inclusion in the study and 6 weeks later, the patients were asked to fill the Roland and Morris questionnaire, which is a validated 24-item questionnaire designed to measure self-rated disability due to back pain (Roland M and Morris R, Spine 8:141–144, 1983). In this questionnaire, the score of the patient is defined as the number of items for which the patient answers "yes" and ranges therefore between 0 (no disability) and 24 (maximum disability).

Statistical analysis

The Roland and Morris scores, measured in each patient before and after 6 weeks of treatment were subjected to a two-way ANOVA analysis for repeated measures, with factors of variation being time (before vs. after treatment) and treatment (placebo vs. crystal insoles). When statistical significance was reached, multiple comparisons were performed using the Student-Newman-Keuls method. P<0.05 was considered statistically significant.

Results and discussion

Figure 7:
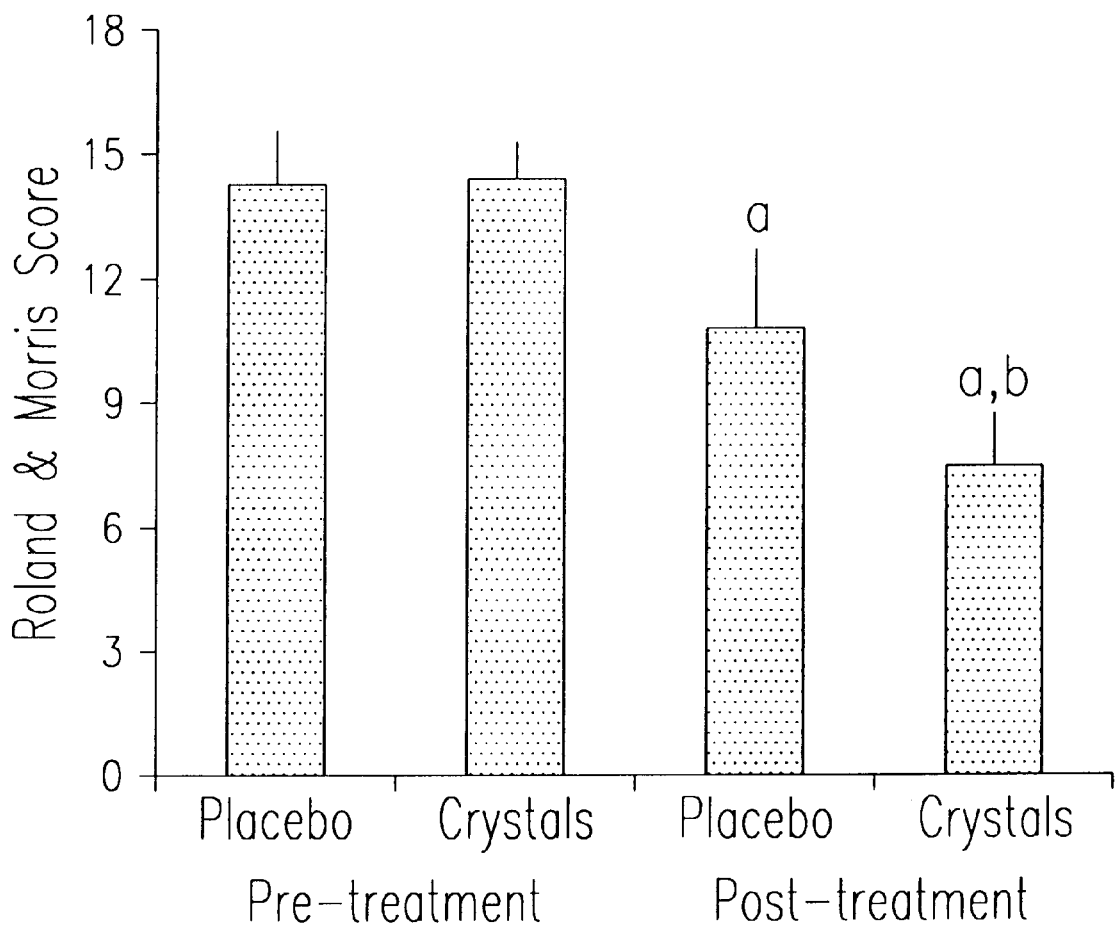
FIG. 7 is a graph of the Roland and Morris statistical analysis of patient's measurements before and after treatment.

A total of 35 patients were included in the study and were randomized into a placebo group (11 patients) and a crystal insole group (24 patients). As shown in FIG. 7, both groups had a similar initial score (mean+SEM: placebo 14.27±1.25 vs. crystals 14.38±0.85, NS). After 6 weeks of treatment, the score was significantly improved in both groups. The score was decreased by 25% in the placebo group to 10.73±2.05 (P<0.02), whereas it was decreased by 49% in the crystal insoles group to 7.50±1.18 (P<0.01). The 49% improvement observed in the crystal insoles group was statistically greater than the 25% improvement observed in the placebo group (P<0.05).

These results show that the crystal containing insoles significantly improved the quality of life of patients with chronic back pain by decreasing their disability condition by 49%. The observed placebo effect (25%) is not surprising in such a clinical study where subjective parameters are measured such as pain, well-being or quality of life. This emphasizes the need to implement double-blind, placebo-controlled studies to evaluate the clinical efficacy of new treatments for chronic back pain.

In conclusion, the crystal insoles are powerful tools that can be used therapeutically to improve the condition of patients with chronic back pain.

Although the invention has been described with respect to specific embodiments, it is understood that modifications are possible within the scope of the appended claims without departing from the spirit of the invention.

We claim:

1. Pedal device for treating and preventing physical troubles associated with statural disequilibrium, which comprises an article adapted to contact a sole of a foot, characterized in that said article incorporates at least a crystalline substance having a color by emitting photons in the wavelength range between about 400 nm and 900 nm stimulating reflex zones located at the sole of the foot.

2. Pedal device according to claim 1, wherein said crystalline substance is in powder form.

3. Pedal device according to claim 1, wherein said article comprises an inner sole to be worn against said sole of a foot.

4. Pedal device according to claim 3, wherein said inner sole is an inner sole of a shoe.

5. Pedal device according to claim 1, wherein said substance is placed at the surface of said article.

6. Pedal device according to claim 1, wherein said article comprises two semi-rigid fabric layers bonded together, said substance being inserted between said layers of said foot sole.

7. Pedal device according to claim 1, wherein crystalline substance is a mineral substance.

8. Pedal device according to claim 1, wherein said crystalline substance is an organic substance.

9. Pedal device according to claim 7, wherein said mineral substance is selected from the group consisting of crystals and powders selected from elements, natural and synthetic sulfides and sulfosalts, natural and synthetic halides, natural and synthetic oxides and hydroxides, natural and synthetic nitrates, carbonates and borates, natural and synthetic sulfates, chromates, molybdates and tungstates, natural and synthetic phosphates, arseniates, and vanadates, natural and synthetic silicates, and natural and organic substances.

10. Pedal device according to claim 7, wherein said mineral substance is selected from the group consisting of sulphur powders.

11. Pedal device according to claim 7 or 8, wherein said crystalline substance is a combination of substances having at least one of the following different colors: red, orange, yellow, green, blue, purple and white.

12. Pedal device according to claim 7, wherein said mineral substance is selected from the group consisting of jasper, cornelian, topaz safranite, aventurine, azurite, amethyst and quartz and mixtures thereof.

13. Pedal device according to claim 7, wherein said mineral substance is disposed between said layers as a plurality of transverse bands of said mineral substances.

14. Pedal device according to claim 1, wherein said substance is disposed at a surface of said article which is in contact with said sole foot.

15. Pedal device according to claim 11, wherein said mineral substance comprises powdered sulphur, said powdered sulphur being incorporated between said fabric layers in amount between about 5 mg to 30 g, at the level of an arch of said foot sole.

16. Pedal device according to claim 15, wherein said crystalline substance comprises a mixture of sulphur powder, red jasper, orange cornelian, yellow topaz safranite, green aventurine, blue azurite, purple amethyst and white quartz.

17. The use of a pedal device to improve the condition of patients suffering from musculoskeletal pain, which comprises placing a pedal device according to claim 1 at one or both feet of said patient.

18. The use of claim 17, wherein the musculoskeletal pain is chronic back pain.

19. The use of claim 17, wherein the musculoskeletal pain is associated with statural disequilibrium.

20. The use of claim 17, wherein said pedal device is applied directly to skin of said sole foot.

21. The use of claim 17, wherein said pedal device is placed over socks or stockings worn by said patient.

22. The use of a pedal device to improve muscle strength and physical performance which comprises placing a pedal device according to claim 1 at one or both feet of a person.

23. The use of claim 22, wherein said person is in need of correction of statural disequilibrium.

24. The use of a pedal device to induce stress relief which comprises placing a pedal device according to claim 1 at one or both feet of a person.

25. The use of claim 24, wherein said person is in need of correction of statural disequilibrium.

* * * * *

UNITED STATES PATENT AND TRADEMARK OFFICE
CERTIFICATE OF CORRECTION

PATENT NO : 6,024,093
DATED : February 15, 2000
INVENTOR(S): Christophe Cron; Thierry Pautrot; Thierry Abribat It is certified that error appears in the above-identified patent and that said Letters Patent are hereby corrected as shown below:

On the title page: Item [30]

- -Foreign Application Priority Data

May 2, 1996 [US] United States      08/642,634--

Signed and Sealed this

Third Day of April, 2001

Attest:

NICHOLAS P. GODICI

*Attesting Officer*      *Acting Director of the United States Patent and Trademark Office*